United States Patent [19]

Uchinami et al.

[11] Patent Number: 4,915,077
[45] Date of Patent: Apr. 10, 1990

[54] AIR-FUEL RATIO CONTROL APPARATUS

[75] Inventors: Masanobu Uchinami; Toshihisa Takahashi, both of Himeji; Hitoshi Inoue, Amagasaki; Shinichi Nishida, Himeji, all of Japan

[73] Assignee: Mitsubishi Denki Kabushiki Kaisha, Tokyo, Japan

[21] Appl. No.: 249,736

[22] Filed: Sep. 26, 1988

[30] Foreign Application Priority Data

Oct. 22, 1987 [JP] Japan ................................. 62-268457

[51] Int. Cl.$^4$ ...................... F02D 41/14; G01N 27/58
[52] U.S. Cl. .................................... 123/440; 123/489; 204/425
[58] Field of Search .................. 123/440, 489, 589; 204/424, 425, 426

[56] References Cited

U.S. PATENT DOCUMENTS

| | | | |
|---|---|---|---|
| 4,665,874 | 5/1987 | Kawanabe et al. | 204/425 X |
| 4,698,209 | 10/1987 | Hashimoto et al. | 204/425 X |
| 4,707,241 | 11/1987 | Nakagawa et al. | 123/489 X |
| 4,753,203 | 6/1988 | Yamada | 123/440 |
| 4,762,604 | 8/1988 | Asakura et al. | 204/425 X |
| 4,765,298 | 8/1988 | Kojima et al. | 123/440 |

*Primary Examiner*—Willis R. Wolfe
*Attorney, Agent, or Firm*—Sughrue, Mion, Zinn, Macpeak and Seas

[57] ABSTRACT

An air-fuel control apparatus comprises an air-fuel ratio sensor comprising a gap portion for introducing exhaust gas generated from an engine, a solid electrolyte oxygen pump for controlling a partial pressure of oxygen in the gap portion and a solid electrolyte oxygen sensor producing an electromotive force in response to a proportion of the partial pressure of oxygen in the gap portion and a partial pressure of oxygen in other than the gap portion. The air-fuel control apparatus is further provided with an electronic control device including a pump current stopping means which controls a pump current from the solid electrolyte oxygen pump so that the electromotive force generated by the solid electrolyte oxygen sensor is maintained at a constant value, and controls not to feed the pump current when the engine is stopped, and a control device which operates the optimum quantity of fuel supply to thereby effect an air-fuel control by a gas mixture producing mean in an operational condition that the engine is not subjected to a feed-back control on the basis of an output signal from the air-fuel ratio sensor, and controls not to feed a pump current by the actuation of the pump current stopping means when the revolution number of the engine is determined to be lower than a predetermined value, i.e. the engine is stopped in an operational condition that the engine is subjected to the feed-back control on the basis of the pump current.

3 Claims, 3 Drawing Sheets

AIR-FUEL RATIO CONTROL APPARATUS

BACKGROUND OF THE INVENTION

1. Field of the Invention

The present invention relates to an air-fuel ratio control apparatus with an oxygen pump type air-fuel ratio sensor formed by an ion conductive solid electrolyte to detect an air-fuel ratio by measuring an oxygen concentration in exhaust gas from an internal combustion engine.

2. Discussion of Background

It has been known to control the engine for, for instance, an automobile at a theoretical air-fuel ratio with use of an oxygen sensor formed by an ion conductive solid electrolyte such as a stabilized zirconia and by detecting a state of burning at a theoretical air-fuel ratio on the basis of the change of an electromotive force produced by the difference between a particle pressure of oxygen in exhaust gas and a partial pressure of oxygen in air. However, although a large output is obtainable when the air-fuel ratio A/F as a proportion in weight of air and fuel is at a theoretical air-fuel ratio of 14.7, there is substantially no change of output in the other area of air-fuel ratio. Therefore, it is impossible to utilize the output of the oxygen sensor when the engine is operated at the air-fuel ratio other than the theoretical air-fuel ratio.

SUMMARY OF THE INVENTION

It is an object of the present invention to provide an air-fuel ratio control apparatus capable of detecting an air-fuel ratio in the area other than a theoretical air-fuel ratio as well as the correct theoretical air-fuel ratio, and of eliminating the deterioration of an air-fuel ratio sensor element irrespective of the operating conditions of an engine.

The foregoing and the other object of the present invention have been attained by providing an air-fuel control apparatus which comprises an air-fuel ratio sensor comprising a gap portion for introducing exhaust gas generated from an engine, a solid electrolyte oxygen pump for controlling a partial pressure of oxygen in the gap portion and a solid electrolyte oxygen sensor producing an electromotive force in response to a proportion of the partial pressure of oxygen in the gap portion and a partial pressure of oxygen in other than the gap portion, an electronic control device including a pump current stopping means which controls a pump current from the solid electrolyte oxygen pump so that the electromotive force generated by the solid electrolyte oxygen sensor is maintained at a constant value, and controls not to feed the pump current when the engine is stopped, and a control device which operates the optimum quantity of fuel supply to thereby effect an air-fuel control by a gas mixture producing mean in an operational condition that the engine is not subjected to a feed-back control on the basis of an output signal from the air-fuel ratio sensor, and controls not to feed a pump current by the actuation of the pump current stopping means when the revolution number of the engine is determined to be lower than a predetermined value, i.e. the engine is stopped in an operational condition that the engine is subjected to the feed-back control on the basis of the pump current.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

Figure 1:
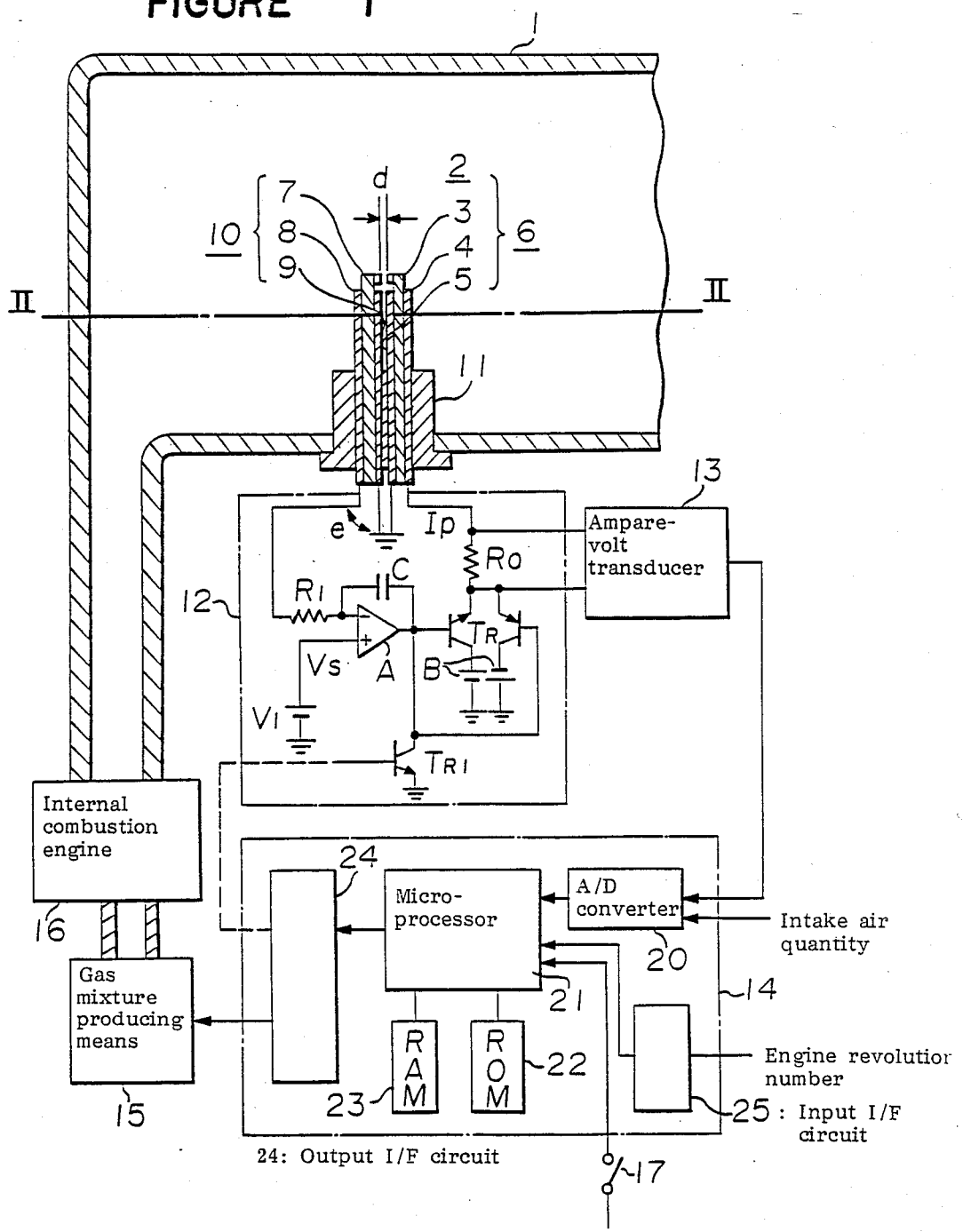
FIG. 1 is a diagram of an embodiment of the air-fuel ratio control apparatus according to the present invention.
Figure 2:
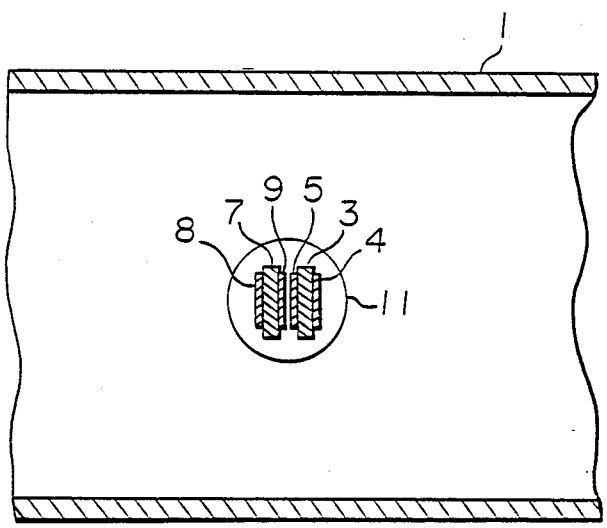
FIG. 2 is a cross-sectional view taken along a line II—II in FIG. 1 which shows an air-fuel sensor used for the embodiment of the present invention.

Referring to the drawings, wherein the same reference numerals designate the same or corresponding parts throughout the several views, and more particularly to FIG. 1 thereof, there is shown schematically an embodiment of the air-fuel ratio control apparatus of the present invention, and a sectional view taken along a line II—II in FIG. 1. In FIGS. 1 and 2, a reference numeral 1 designates an exhaust pipe for an engine and a numeral 2 designates an air-fuel ratio sensor disposed in the exhaust pipe 1.

The air-fuel ratio sensor 2 comprises a solid electrolyte oxygen pump 6 (hereinbelow, referred to as an oxygen pump) which is constituted by a flat ion conductive solid electrolyte (stabilized zirconia) plate 3 having a thickness of about 0.5 mm and electrodes 4, 5 made of platinum attached to both side surfaces of the plate 3, a electrolyte oxygen sensor 10 (hereinbelow, referred to as an oxygen sensor) which is constituted by a flat ion conductive solid electrolyte plate 7 and electrodes 8, 9 made of platinum attached to both side surfaces of the plate 7 in the same manner as the oxygen pump 6 and a supporting block 11 to support the oxygen pump 6 and the oxygen sensor 10 so that they face with a minute gap d of about 0.1 mm.

A numeral 12 designates an electronic control apparatus which is constituted in such a manner that an electromotive force e produced between the electrodes 8, 9 of the oxygen sensor 10 is applied to an reversing input terminal (negative) of an operational amplifier A through a resistor $R_1$. A transistor TR is actuated by the output of the operational amplifier A which is in proportion to the difference between a reference voltage $V_s$ (obtained by a power source $V_1$) applied to a non-reversing input terminal (positive) of the operational amplifier A, whereby a pump current $I_p$ flowing between the electrodes 4, 5 of the oxygen pump 6 is controlled. Namely, the electronic control apparatus 12 functions to supply the pump current $I_p$ necessary to keep the electromotive force e at a predetermined value of $V_s$.

The transistor TR is constituted by a pair transistors TR. The collectors of the transistors TR are respectively grounded through respective power sources B, and the emitters are used commonly to be connected to the electrode 4 of the oxygen pump 6 through a resistor $R_o$. Both ends of the resistor $R_o$ is connected to input ends of an ampere-volt transducer 13.

The resistor $R_o$ is to produce an output signal corresponding to the pump current $I_p$ supplied from the direct power sources B as a pump current supplying means.

The bases of the transistors TR are connected to the collector of a transistor TR 1. The emitter of the transistor TR 1 is grounded and the base is connected to an output interface circuit 24. The transistor TR 1 is to control the pump current being to be stopped or supplied. The transistor TR 1 forms a pump current stopping means and is controlled by a control device 14 which is described below. A capacitor C is connected between the output terminal of the operational amplifier A and the reversing input terminal of the amplifier A. The detail of the control device 14 will be described.

A numeral 20 designates an AD converter for converting an analogue output from the ampere-volt transducer 13 and information of intake air quantity into digital values, a numeral 21 designates a micro-processor for effecting arithmetic operations and logical treatments in accordance with programs stored in an ROM 22, a numeral 23 designates an RAM temporally storing values operated by the micro-processor 21, a numeral 24 an output interface circuit which receives a result of the arithmetic operations and the logical treatments of the micro-processor 21, and outputs a signal to actuate the pump current stopping means in the electronic control device 12 and a signal to control an amount of fuel supplied to a gas mixture producing means 15 or an amount of intake air, and a numeral 25 designates an input interface circuit for receiving a signal indicative of an engine revolution number from a crank angle sensor (not shown). In FIG. 1, a nemeral 16 designates an internal combustion engine and a numeral 17 designates a key switch.

Figure 3:
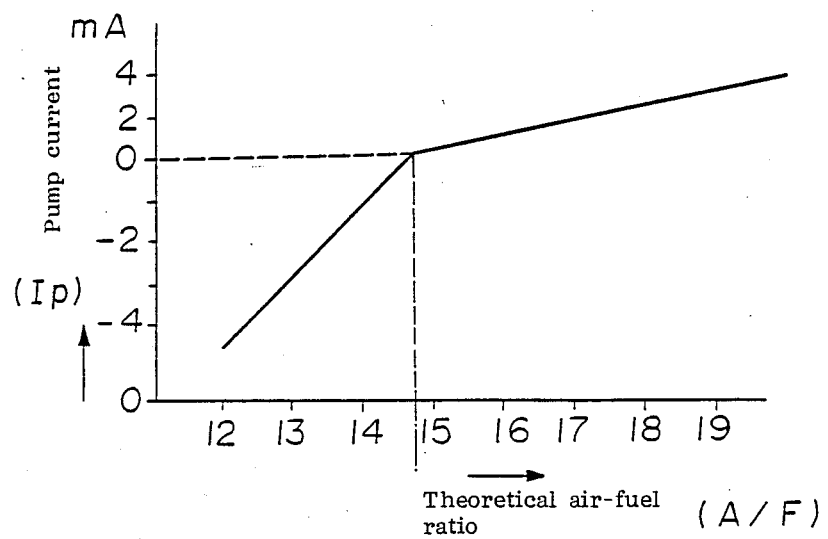
FIG. 3 is a characteristic diagram of the air-fuel ratio sensor shown in FIG. 2.

FIG. 3 shows the relation between an air-fuel ratio and a current supplied from an oxygen pump in the case that an air-fuel ratio sensor 2 is attached to a gasoline engine.

In the characteristic diagram of FIG. 3, the reason why the pump current $I_p$ varies in proportion to an air-fuel ratio in the region of air-fuel ratio A/F greater than a theoretical air-fuel ratio is described in Japanese Unexamined Patent Publication No. 130649/1981. Namely, an electromotive force e is produced in the oxygen sensor 10 when a partial pressure of oxygen contained in exhaust gas in the minute gap portion d is different from a partial pressure of oxygen in the exhaust gas flowing in the exhaust pipe 1. A pump current $I_p$ varies in proportion to an concentration of oxygen in the exhaust gas when the pump current $I_p$ supplied to the oxygen pump 6 is controlled so that the electromotive force e approaches a predetermined value. Since the air-fuel ratio is substantially in proportion to the oxygen concentration, the pump current $I_p$ varies in proportion to the air-fuel ratio A/F.

Referring to FIG. 3, the change of the pump current $I_p$ in the region of values smaller than the theoretical air-fuel ratio is likely caused by the fact that the air-fuel ratio sensor 2 is sensitive to the concentration of carbon monoxide (CO) in the exhaust gas.

In the function of the electronic control device 12, there is no problem when the gasoline engine normally operates. However, when the engine is stopped, or becomes a conductive state by the actuation of the key switch 17 to start the engine and then, it is left for a while, the electronic control device 12 increases the supply of the pump current $I_p$ so that the electromotive force e of the oxygen sensor 10 is kept at a predetermined value $V_s$. However, because of the engine stopped, there is too much amount of oxygen in comparison with the operation of the engine, whereby the value of the pump current $I_p$ becomes large. When such condition continues for a long time, the stabilized zirconia forming a part of the oxygen pump 6 or the electrodes to take out the pump current become deteriorated, whereby it is impossible to use it as a sensor.

In view of the above-mentioned, the present invention is to prevent the elements of the air-fuel ratio sensor from deteriorating irrespective of the operational conditions of the engine and to block a pump current by detecting the stop of the engine.

Specifically, a pump current $I_p$ is converted to have a voltage level by the ampere-volt transducer 13 and the output signal of the ampere-volt transducer 13 is supplied to the control device 14 and then, the control device 14 supplies a signal to the gas mixture producing means 15. The control device 14 receives a signal indicative of a revolution number of engine to detect a state of engine stop, and an output signal is supplied to the electronic control device 12 to stop the pump current.

The operation of the air-fuel ratio control apparatus of the present invention will be described.

In the operational condition that a feed-back control with use of the air-fuel ratio sensor 2 is not conducted, an analogue value indicating information of intake air quantity is converted into a digital value by the AD converter 20, and the micro-processor 21 operates to obtain the optimum quantity of fuel supply by using steps and constants which are previously stored in the ROM 22.

Data obtained by the operations are supplied to the gas mixture producing means 15 through the output interface circuit 24. The data obtained by the operations correspond to the width of a driving pulse signal for an electromagnetic fuel injection valve 15 provided in the gas mixture producing means 15, whereby control of the air-fuel ratio is carried out by the gas mixture producing means 15.

In the operational condition that a feed-back control is conducted in accordance with the output of the air-fuel ratio sensor 2, i.e. by the pump current $I_p$, the operations conducted without the feed-back control, i.e. an opened loop control are corrected by the pump current $I_p$. In this case, the correction includes an appropriate ripple in a PI (proportioning and integrating) control.

Figure 4:
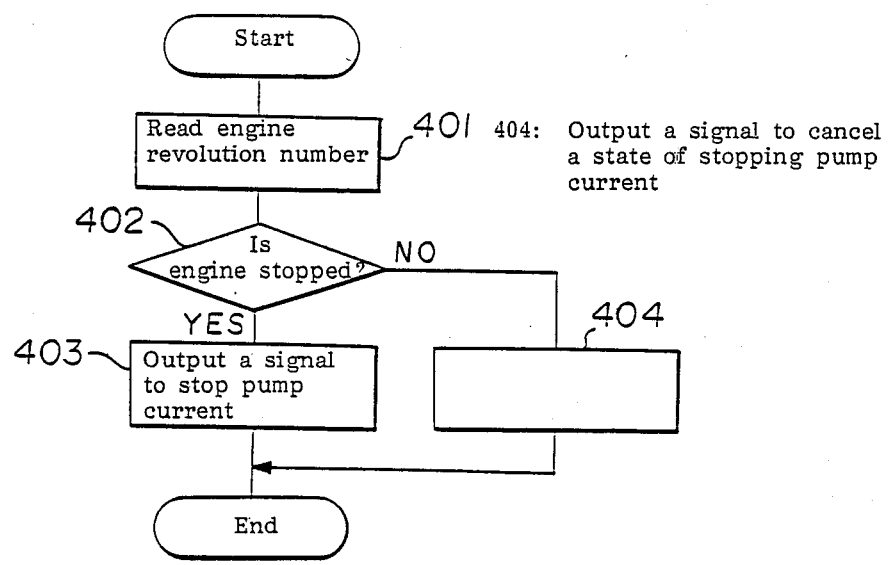
FIG. 4 is a flow chart showing a series of steps for operating the air-fuel ratio control apparatus of the present invention.

Control of the pump current from the air-fuel ratio sensor 2 is described with reference to FIG. 4. When the key switch 17 is turned on at the starting time of the operation of an automobile, the number of revolution of the engine is detected at Step 401. At Step 402, determination is made as to whether or not the revolution number is higher than a predetermined value such as 30 rpm. When a detected value is lower than the predetermined value, determination is made so that the engine is stopped. When it is the case, the Step 403 is taken. When it is not the case (higher than 30 rpm), Step 404 is taken.

At Step 403, an output signal for stopping the pump current is supplied from the micro-processor 21 through the output interface circuit 24 to the transistor TR 1 in the electronic control device 12 to thereby change a potential at the basis of the transistors TR to the ground potential so that the pump current $I_p$ is stopped.

At Step 404, an output signal for supplying the pump current $I_p$ in correspondence to a detected air-fuel ratio is supplied from the micro-processor 21 through the output interface circuit 24 to the transistor AR 1 in the same manner as the Step 403.

Thus, in the air-fuel ratio control apparatus using an air-fuel ratio sensor in which an output is changed in proportion to an air-fuel ratio to thereby effect a feed-back control of a gas mixture introduced in an internal combustion engine of the present invention, a pump current from an oxygen pump is stopped by actuating a pump current stopping means in an electronic control device on the basis of the output of a control device when the engine is found to be stopped by detecting the number of revolution of the engine. Accordingly, deterioration of an air-fuel ratio sensor element can be eliminated irrespective of the operational conditions of the engine.

Obviously, numerous modifications and variations of the present invention are possible in light of the above teachings. It is therefore to be understood that within the scope of the appended claims, the invention may be practiced otherwise than as specifically described herein.

What is claimed is:

1. An air-fuel control apparatus which comprises:
an air-fuel ratio sensor comprising a gap portion for introducing exhaust gas generated from an engine, a solid electrolyte oxygen pump for controlling a partial pressure of oxygen in said gap portion and a solid electrolyte oxygen sensor producing an electromotive force in response to a proportion of the partial pressure of oxygen in the gap portion and a partial pressure of oxygen in other than said gap portion,
an electronic control device including a pump current stopping means which controls a pump current from said solid electrolyte oxygen pump so that the electromotive force generated by said solid electrolyte oxygen sensor is maintained at a constant value, and controls not to feed the pump current when said engine is stopped, and a control device which operates the optimum quantity of fuel supply to thereby effect an air-fuel control by a gas mixture producing mean in an operational condition that said engine is not subjected to a feed-back control on the basis of an output signal from said air-fuel ratio sensor, and controls not to feed a pump current by the actuation of said pump current stopping means when the revolution number of said engine is determined to be lower than a predetermined value, i.e. the engine is stopped in an operational condition that said engine is subjected to the feed-back control on the basis of the pump current.

2. The air-fuel ratio control apparatus according to claim 1, wherein said electromotive force produced by said air-fuel ratio sensor is kept to a predetermined constant value by means of an operational amplifier and a reference voltage power source.

3. The air-fuel ratio control apparatus according to claim 1, wherein said control device is adapted to receive a voltage signal which is converted from a pump current by an ampere-volt transducer to thereby actuate a gas mixture producing means, and to receive a signal indicating an engine revolution number to thereby output a signal to said electronic control device to stop to the pump current.

* * * * *